Figure 1:
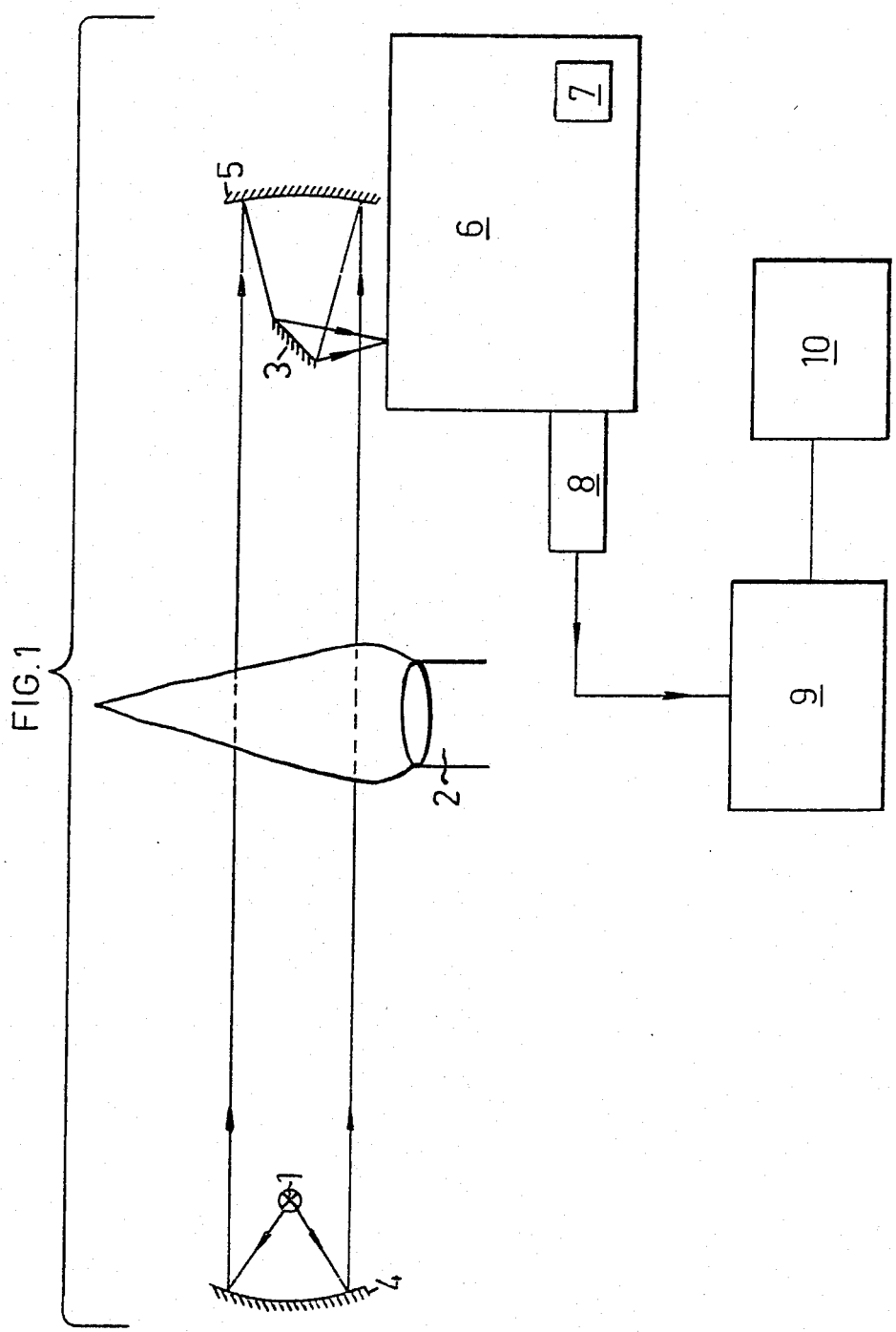

United States Patent [19]

Unéus et al.

[11] Patent Number: 4,790,652
[45] Date of Patent: Dec. 13, 1988

[54] METHOD AND APPARATUS FOR DETERMINING PARAMETERS OF GASEOUS SUBSTANCES

[75] Inventors: Leif Unéus; Svante Wallin, both of Lund, Sweden

[73] Assignee: Opsis AB, Lund, Sweden

[21] Appl. No.: 30,838

[22] PCT Filed: Jun. 12, 1986

[86] PCT No.: PCT/SE86/00282
§ 371 Date: Feb. 4, 1987
§ 102(e) Date: Feb. 4, 1987

[87] PCT Pub. No.: WO86/07455
PCT Pub. Date: Dec. 18, 1986

[30] Foreign Application Priority Data
Jun. 13, 1985 [SE] Sweden .................. 8502946

[51] Int. Cl.$^4$ .................. G01J 5/58; G01J 3/06; G01J 3/32
[52] U.S. Cl. .................. 356/45; 356/308; 356/315; 356/328
[58] Field of Search .............. 356/45, 307, 308, 310, 356/326, 328, 315

[56] References Cited

U.S. PATENT DOCUMENTS 2,406,318 8/1946 Brace .
3,565,567 2/1971 Rains .
4,214,835 7/1980 Roos .................. 356/306
4,411,519 10/1983 Tagami .................. 356/45

FOREIGN PATENT DOCUMENTS 0121404 10/1984 European Pat. Off. .

OTHER PUBLICATIONS

Albrechcinski et al., "Rapid-Scan Instrumentation for Spectrally & Spatially Resolved Radiance Measurements of Short-Duration Rocket Plumes", Conference ICIASF 79, Monterey, Ca., Sep. 79, pp. 57–71.
Derwent's abstract nr 03281 E/02, SU 639-320, (Irkut Univ Appld Ph), 1 Dec. 1976, (Shin Nippon Seitetsu K K), 28 May 1983.
Applied Optics and Optical Engineering, R. Kingslake, vol. V. 1969, "Grating Monochromators", p. 80.

Primary Examiner—Vincent P. McGraw
Attorney, Agent, or Firm—Merchant, Gould, Smith, Edell, Welter & Schmidt

[57] ABSTRACT

A method for determining parameters, especially pressure, temperature, concentration, number of particles and particle size distribution, of gaseous substances present in combustion processes and other high temperature processes, comprises transmitting spectrally broad-band light through an object (2) of measurement, spectrally dividing the light transmitted through said object, and recording the spectral distribution of the light in the studied wavelength range a large number of times. Each recording occurs sequentially in that the spectrally divided light is swept relative to a one-channel detector and for such a short time that the total light intensity of the entire wavelength range is constant during each recording. After that, the mean value of said recorded spectral distributions is generated, and the required parameters are calculated on the basis of said mean value spectral distribution, the appearance of said means value spectral distribution, as well as spectra calculated or recorded for known conditions, being utilized for said calculation.

An apparatus comprises means for carrying out the method.

3 Claims, 6 Drawing Sheets

METHOD AND APPARATUS FOR DETERMINING PARAMETERS OF GASEOUS SUBSTANCES

The present invention relates to a method and an apparatus for determining parameters, especially pressure, temperature, concentration, number of particles and particle size distribution, of gaseous substances present in combustion processes and other high temperature processes, in which method light transmitted through or reflected or emitted by the gases is spectrally divided, and the spectral distribution of the light in the studied wavelength range is recorded a large number of times.

The rise in raw material prices and the increasing insistence on efficient measures against pollution have intensified the interest in, for example, combustion control. An American study from the middle of the 1970's shows for example that, if the efficiency of combustion processes could be increased by 1%, this would mean a saving of 15 million barrels of oil per annum in the USA alone. The combustion in coal-burning power plants is another example of a combustion process where an efficient control could save large sums of money. Thus, if the temperature in a coal-burning power plant becomes too high, slag products are deposited which, if it comes to the worst, may necessitate closing down the entire plant for cleaning. Furthermore, the emission of substances hostile to the environment could be reduced if some combustion processes could be controlled more efficiently, for example the incineration of refuse. If the combustion temperature becomes too high (above 1600° C.) large amounts of NO are generated, which is one of the substances considered to contribute to the so-called forest kill. If, on the other hand, the temperature is too low, dioxine is formed which, is a dreaded environmental poison. Suitable control measures to maintain the temperature at an intermediate value can minimise the emission of these two dangerous substances.

However, to be able to conveniently control the above-mentioned and other processes, transducers are required by which the control parameters, such as the temperature, the concentration of specific substances etc., can be determined.

Unfortunately, the technical progress in this field has not kept pace with the rise in raw material prices and the environmental issues. One reason is, of course, the high temperatures which render the use of conventional transducers and measuring instruments impossible. Another reason is that the measuring environment in, for example, a coal-burning power plant places high demands on the measuring equipment which must be unsusceptible to dirt, vibrations etc. A third reason is the turbulent character of the measuring environment, i.e. the measuring conditions are subject to strong variations in time, which makes it difficult to design a measuring equipment capable of operating with great accuracy and reliabilty, and up to a few years ago only unreliable methods were available for determining temperature, concentration and other parameters. For example, the temperature was measured by means of thermocouples which interfered with the processes and therefore did not give reliable results. Furthermore, the concentration of the substances present during combustion was recorded by exhausting gas from the combustion zone and injecting it into, for example, a mass spectrometer. Also these concentration measurements were unreliable because exhausting of the sample interfered with the processes, the exhausted gas sample was cooled in the mass spectrometer, and there was a risk that the substances could interreact in the mass spectrometer so that the substances measured were different from those which were present during the process.

When it is desired, in other technical applications, to prevent the measurement from interfering with the process, use is frequently made of optical measuring techniques. One group of optical measuring techniques is based on the principle of developing by means of light a secondary effect, for example fluorescence, which carries information about the required parameter and the intensity of which is measured. Examples of such techniques are Raman spectroscopy, laser induced fluorescence etc. However, these techniques are not readily applicable to full-scale combustion plants because the secondary effect is drowned in the light from the flame.

The only realistic possibility of using optical measuring techniques in combustion plants is to make absorption measurements, i.e. to measure how much light is absorbed by the flame. Also this technique is difficult because the particle density in these environments is very high and the light transmission therefore very low. In a normal combustion plant boiler, the transmission is less than 1%, for which reason a very strong light source is required in order to provide a useful measuring signal.

Recently, an optical technique has been developed by which non-contact measurement of concentration and temperature in combustion processes can be carried out. This technique which is termed CARS (Coherent Anti-Stokes Raman Scattering) is presented in "Elteknik med aktuell elektronik", 1985:4, pp. 76–80. For CARS measurements, use is made of two lasers, one of which is tunable and the other has a fixed frequency. The beams from these two lasers are focused and adjusted such that they intersect at a specific angle. The area upon which the two laser beams are to be focused has a surface of some $\mu m^2$. If the focusing does not succeed, the technique does not work. Furthermore, the frequency difference between the beams must exactly correspond to the difference between two internal energy levels in the molecule one wishes to examine. As will be immediately apparent from this brief description, the measuring device here concerned is technically highly complicated and can be installed and operated by specially trained technicians only. Naturally, such a device is highly expensive; the paper mentions the sum of 2 million Swedish crowns for each system, and since these are high-power lasers, this sum is not expected to become much lower.

Unfortunately, laser technique also has other shortcomings. Firstly, it may prove difficult to produce a sufficiently strong measuring signal if measurement is carried out in processes having a high particle content because also the CARS technique utilises secondary light for detection. Secondly, the laser is a noisy light source, and this means that the measuring accuracy in many cases will not be very good. Thirdly, different measuring setups (lasers) must be used for measurement in different frequency ranges. Fourthly, safety problems arise since light reflected from surfaces reflecting as little as a few percent may cause irreparable damage to the eye.

For measurements in combustion processes and other high temperature processes there thus is a need for a simpler, more reliable and less expensive technique which can be utilised by anyone without expert knowledge but which nevertheless stands up to the severe conditions encountered in an environment with high temperatures and a high degree of pollution.

A cheaper and less complicated concentration measuring technique which is used in, for example, chemistry and biology, is the absorption spectroscopy. This technique involves irradiating a cuvette containing a liquid measuring sample with white light, and recording sequentially, by means of a slow-scanning spectrometer, the intensity of the different wavelengths in the spectrum. A typical scan lasts a few minutes, but this is no problem because the measuring environment is not turbulent.

A device utilising this technique and capable of measuring in turbulent environments is disclosed in European patent application No. 84302093.4. This device comprises a pulsed light source for transmitting light pulses towards the sample whose concentration is to be measured, a spectrometer for dividing each light pulse transmitted through the sample into at least two predetermined spectral components, a diode array for generating output signals corresponding to the light intensity of each of said predetermined spectral components, and a mean value generator for calculation for all light pulses of the mean value of the difference in the intensity of the transmitted light for the said two spectral components.

In this device, the influence of turbulence thus is eliminated by making use of a pulsed light source, but this brings the disadvantage that it is difficult to compare spectra taken during different pulses because the spectral distribution of the light from the light source varies from one pulse to another.

A further disadvantage of this device is that it is difficult to record a spectrum with an acceptable signal-to-noise ratio. One reason for this is the manner in which the spectrum is recorded, i.e. by means of a diode array. In principle, a diode array comprises a large number of juxtaposed detector elements. These detector elements suffer from the disadvantage that, because of their design, they have a limited light sensitivity and, furthermore, are mutually different in respect of dark current, amplification, temperature-dependent drift, and drift due to aging. As a result of these factors, the above-mentioned device is unsuitable for the determination of hightemperature process control parameters.

It therefore is the object of the present invention to provide an inexpensive and simple method for high-precision measurement of parameters of gaseous substances occurring in combustion processes and other high-temperature processes. An especially interesting application is measuring inside flames. Another object of this invention is to provide an apparatus for carrying the method into effect.

The object of the invention is achieved by means of a method which is characterised in that each recording occurs sequentially in that the spectrally divided light is swept relative to a one-channel detector and for such a short time that the total light intensity of the entire wavelength range is constant during each recording; that the means· value of said recorded spectral distributions is generated; and that the required parameters are calculated on the basis of said mean value spectral distribution, the appearance of said mean value spectral distribution, as well as spectra calculated or recorded for known conditions, being utilised for said calculation.

To carry the method according to the invention into effect, use is made of an apparatus which is characterised by means for sequential recording of the spectral distribution of the light in the studied wavelength range in such a short time that the total light intensity of the entire wavelength range is constant during each recording, said means comprising a one-channel detector whose output signal is proportional to the intensity of the received light, and means for sweeping the spectrally divided light relative to said one-channel detector; a mean value generator; and computer means for calculating the required parameters.

The main advantage of the method and the apparatus according to the invention is that the spectrum is recorded by means of a one-channel detector, whereby the measuring errors associated with the different characteristics of the detector elements in a diode array are eliminated. A further advantage is that the detector element employed may be a photomultiplier having a higher light sensitivity than the detector elements of the diode array.

If measuring is effected on transmitted or reflected light, the apparatus further comprises a spectrally broad-band continuous light source transmitting light towards the object of measurement. The advantage of a continuous light source resides in that it can be made immensely stable, and that it is more reliable than, for example, a pulsed lamp.

Otherwise, the object of measurement itself is used as a light source, and then the emission spectra are investigated.

The present invention makes it possible to carry out measurement on all gaseous substances through which light can be transmitted.

Furthermore, the parameters of several substances may be determined in one and the same measurement, which is of course an advantage.

Because a large number of spectra are recorded, and because each spectrum is recorded during a time which is so short that the conditions of measurement are constant, very small absorptions can be detected.

Figure 2:
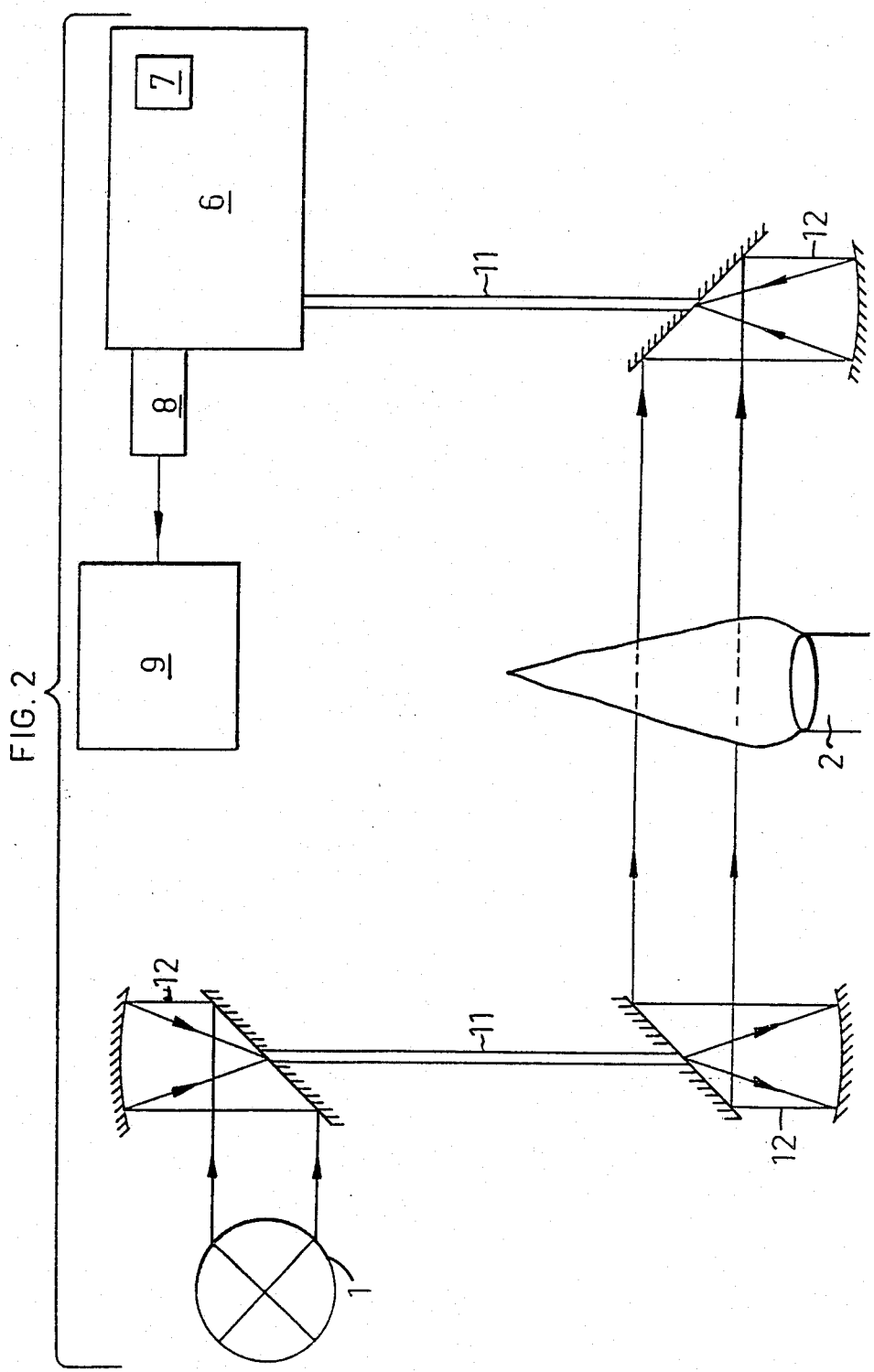
Figure 3A:
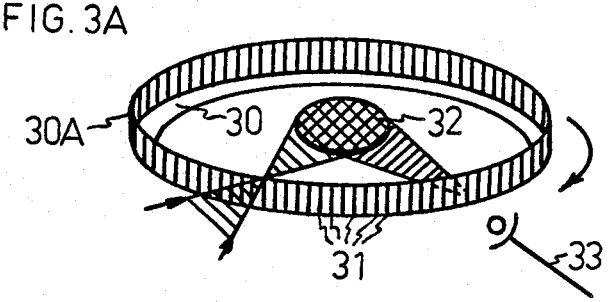
Figure 3B:
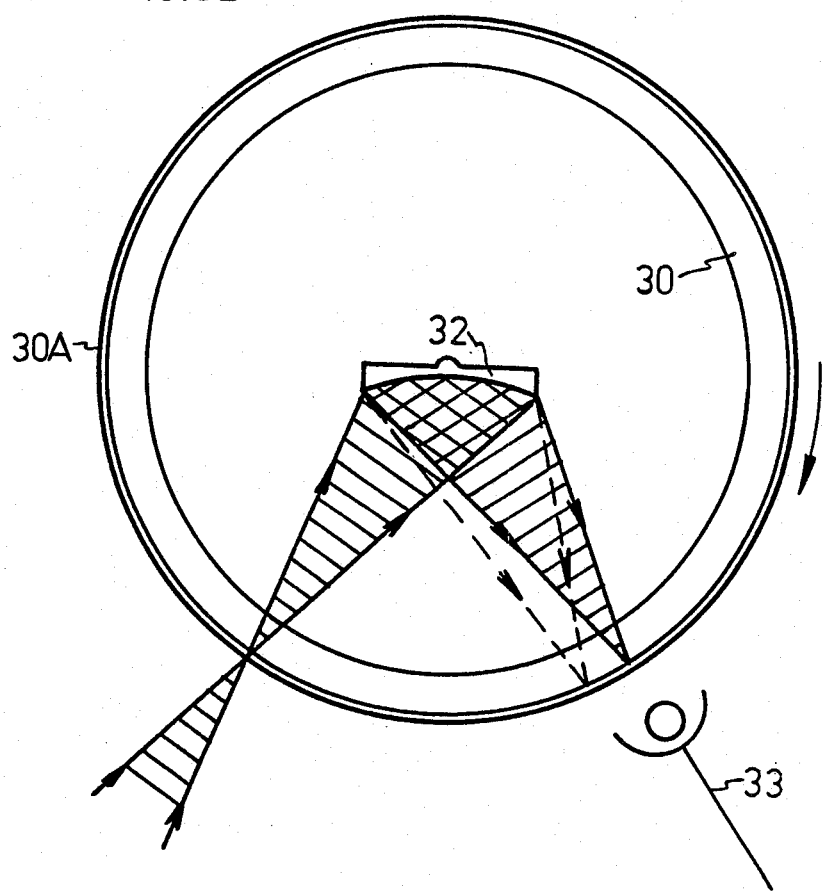
Figure 4:
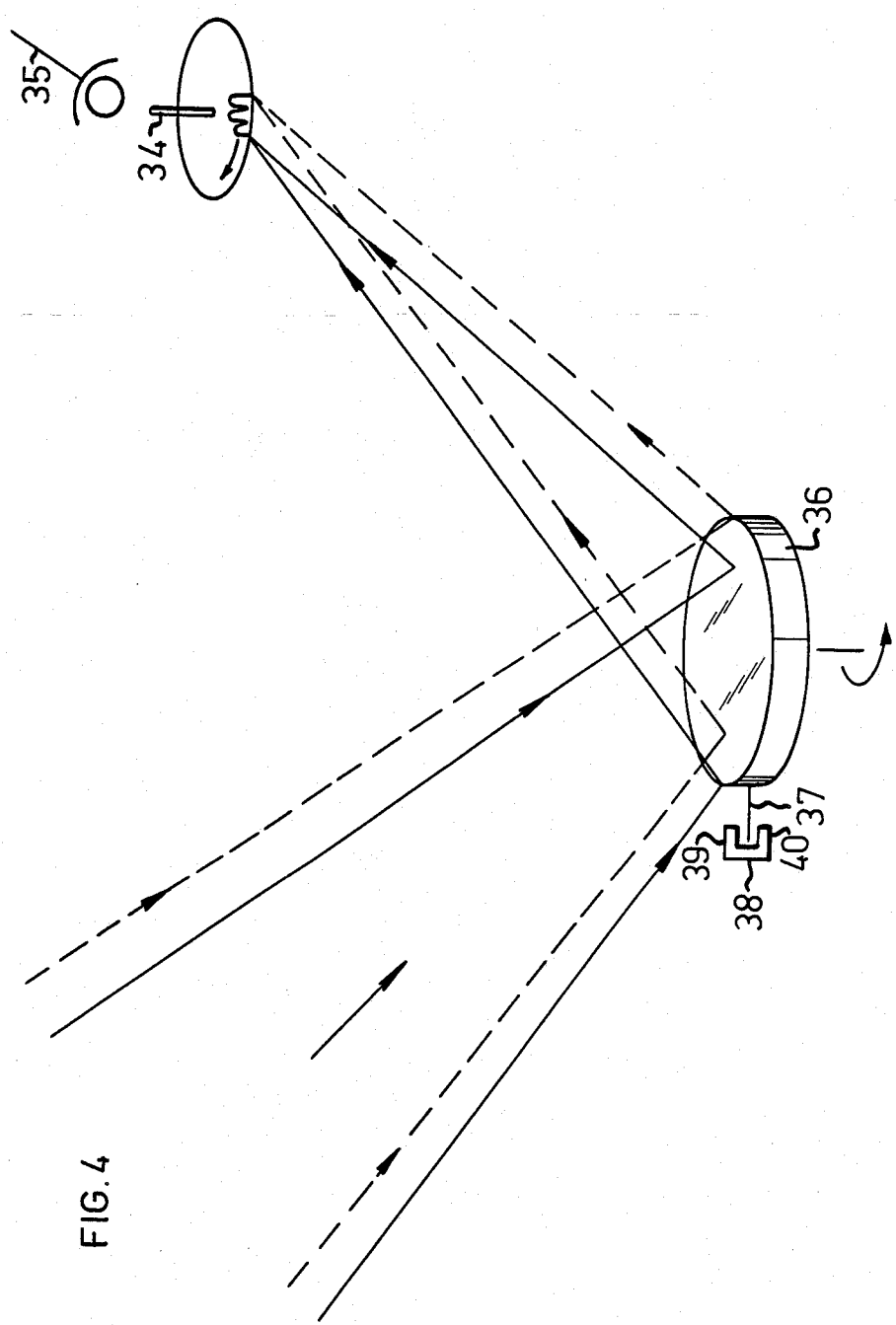
Figure 5A:
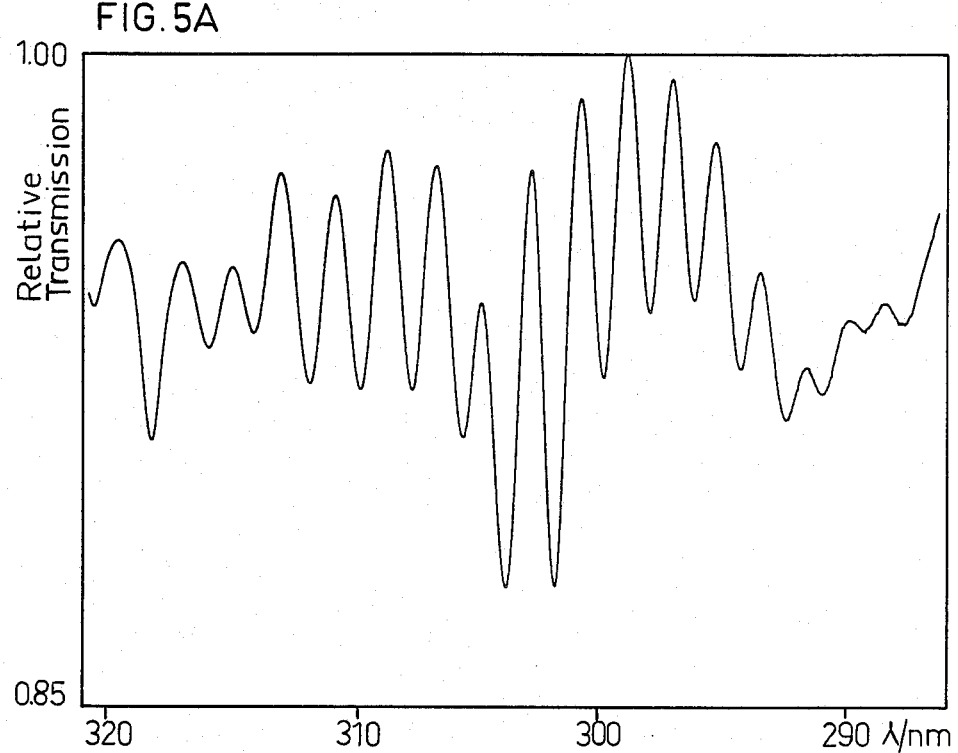
Figure 5B:
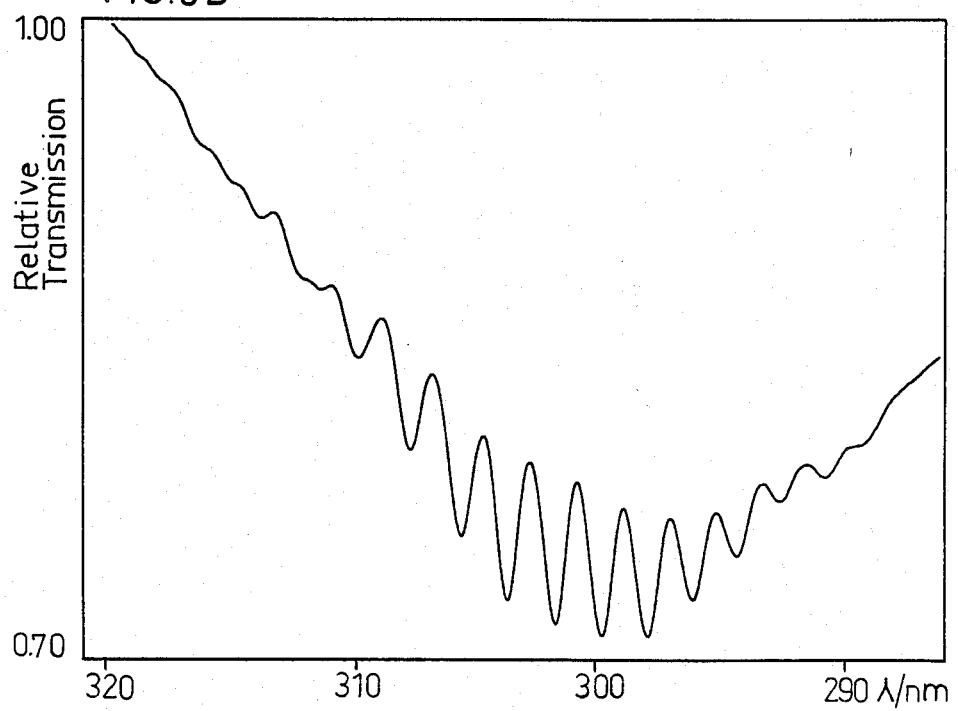
Figure 6:
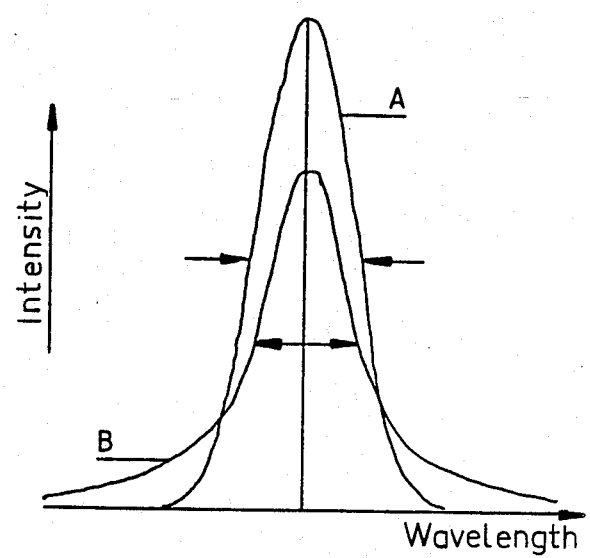

A number of embodiments of the invention will be described below, reference being had to the accompanying drawings. FIG. 1 illustrates schematically an apparatus according to the invention. FIG. 2 illustrates schematically a variant of the apparatus shown in FIG. 1. FIGS. 3A and 3B illustrate schematically, in perspective and from above, respectively, an apparatus for sequential scanning of a spectrum. FIG. 4 illustrates schematically an apparatus for sweeping a spectrum across a detector. FIGS. 5A and 5B illustrate absorption spectra of one and the same substances, recorded at different temperatures. FIG. 6 is an absorption profile and illustrates the profile broadening depending upon temperature and pressure.

FIG. 1 illustrates an apparatus adapted for measuring the parameters of gases present in combustion processes and other high temperature processes. A lamp 1 which must have at least the same frequency range as the wavelength range one wishes to investigate, which must be continous and as stable as possible, and which may be, for example, a 450 watt xenon lamp, is positioned in the focus of a parabolic mirror 4 and adjacent the object 2 which is to be measured. Opposite the lamp 1 and on the far side of the object 2, which here is a flame, a receiving device comprising a parabolic mirror 5 and an oblique mirror 3 is provided. If measuring is effected on light reflected or emitted by the object of measurement, the receiving device may be positioned elsewhere in relation to the lamp. A spectrometer 6 for spectral division of the light is positioned such that it receives the light from the receiving device. Alternatively, the light from the object of measurement may be conducted directly into the spectrometer 6, in which case the receiving device will be superfluous. For measurements within the visible region and within the IR and UV regions, the spectrometer suitably is a conventional grating spectrometer. The apparatus further comprises means 7, 8 for sequential recording of the light spectrally divided by the spectrometer 6. In this embodiment, the said means include a rotary mirror 7 sweeping the spectrum across a fixed output slit from the spectrometer, as well as a light detector 8 which is disposed behind said output slit and preferably is a photomultiplier, for conversion of the intensity of the light transmitted through said slit, into electrical signals. In this instance, the spectrum thus is swept across a fixed slit, but it will be appreciated by those skilled in the art that the slit may just as well be swept across a stationary spectrum. In both cases, scanning is carried out such that the location of the slit in the space relative to the spectrum is changed by mechanical means. FIGS. 3 and 4 below describe examples of suitable recording means. A further condition that must be fulfilled by said recording means 7, 8 is that the spectrum can be recorded so quickly that the total light intensity of the entire wavelength range will be constant during each recording. On the other hand, the total light intensity may be different at different recordings because the signal level fluctuates in dependence on any turbulence in the object of measurement, vibrations etc. The output of the apparatus is connected to a high-speed A/D converter, converting the analog signal from the photomultiplier into digital format, whereupon the signal is stored in a computer 9. Stored in the computer 9 are programs for generating means values of the recorded spectra recorded under known conditions. and for controlling the rotary mirror 7 as well as reference spectra recorded under known conditions. The computer also has a memory space for storing the recorded spectra. A printer 10 or some other suitable display unit may be connected to the computer. Furthermore, the computer 9 may be connected to control means (not shown) receiving control signals in response to the measuring result.

The measuring apparatus operates as follows. Light from the lamp 1 is reflected in the parabolic mirror 4 which it leaves in the form of a parallel luminous beam which is transmitted through the object 2 to be measured. The light transmitted is received by the parabolic mirror 5, is reflected to the oblique mirror 3 and on to the input of the spectrometer 6. In the spectrometer 6, the light is spectrally divided. The rotary mirror 7 sweeps the spectrum across the fixed slit on the spectrometer output, and the photomultiplier 8 sequentially receives the light coming from the different wavelength ranges of the spectrum and transmitted through the slit, and provides an analog signal corresponding to the intensity of this light. The analog signal is A/D converted and stored in the computer 9. By repeating these operations, a large number of spectra (10,000-100,000) are recorded in a short time, whereupon the mean value of these spectra is calculated in the computer. To compensate for wavelength-depending variations in the output signal of the lamp and the reflection in mirrors etc., and to produce the interesting absorption profiles, the mean value spectrum is divided by a suitable function. On the basis of the spectrum thus obtained, the computer calculates the required parameters in real time, as will be explained below.

FIG. 2 illustrates a variant of the installation in FIG. 1. According to this variant, the light is conducted from the light source 1 to the object 2 to be measured and/or from said object 2 to the spectrometer 6 by means of optical fibres 11. The light is introduced into the optical fibres by means of a special device 12 comprising a planar oblique mirror and a focusing mirror (patent applied for, SE No. 8406025-0). This measuring installation is intended primarily for measurements in environments difficult of access, and for measuring across short and well-defined distances, for example inside a flame.

FIGS. 3A and 3B illustrate an example of an apparatus for sequential recording of a spectrum. The apparatus comprises a rotary disk 30 which is provided along its periphery with an upstanding ledge 30A with slits 31 which are parallel to the axis of rotation of the disk 30 and which are equidistantly spaced apart. Furthermore, a focusing grating 32 is mounted in the centre of the disk 30, and a photomultiplier 33 is mounted behind the ledge 30A.

Upon use of the apparatus, the disk 30 is caused to rotate by means of a motor (not shown), and the light is caused to impinge on a point above the ledge 30A through a fixed slit (not shown) located at the point of intersection of the light rays, and on to the focusing grating 32 which spectrally divides the light and reflects it against the periphery. In this manner, one slit 31 at a time will move through the spectrum, and the photomultiplier 33 will sequentially receive and record light of the different wavelengths of the spectrum. The advantage of this arrangement is that the slits 31 on the ledge 30A all the time will lie in the focal plane of the focusing grating 32.

FIG. 4 illustrates another apparatus for the sequential recording of a spectrum, said apparatus comprising a rotary mirror 36 located within the spectrometer 6 and receiving the spectrally divided light. The normal to the rotary mirror 36 deviates slightly from the axis of rotation of the mirror. When the mirror is rotated by means of a motor (not shown), the incident light is reflected in an elliptical path on the output slit 34 of the spectrometer 6, behind which slit a photomultiplier 35 is provided for sequentially receiving light from the different wavelengths of the spectrum. Furthermore, the apparatus comprises a pin 37 provided at the periphery of the rotary mirror 36 and extending radially from said mirror, as well as a light barrier 38 comprising an optical transmitter 39 and receiver 40. The light from the transmitter 39 is stopped when the pin 37 passes, whereby a trigger signal for the measuring is generated.

The calculations made in the computer are based on the fact that electrons can move only in specific shells or orbits in atoms. Each electron orbit corresponds to a specific energy state. The situation is rather more complicated in molecules. Besides the electron states occurring in the atoms, there exist also vibrational and rotational states which are due to the fact that the molecules can vibrate along and rotate about, respectively, an axis. The principle, however, is the same: each molecule has a limited number of permissible energy states. If an atom or a molecule is struck by photons, i.e. by light whose frequency exactly corresponds to the energy difference between two states in the atom or molecule, a photon is absorbed with some probability, in which case the atom or molecule passes from one energy state to another. By transmitting light of a specfic frequency content and a specific intensity through, for example, a gas, and by studying how much light has been absorbed at a specific frequency during transmission through the gas, much information is obtainable about the substances contained in the gas.

A review of how concentration, temperature, pressure, particle size distribution and number of particles are calculated on the basis of the recorded spectra, will be given below.

TEMPERATURE

The electrons in an atom occupy different states depending upon the temperature. In the same manner, different electron, vibrational and rotational states in a molecule are occupied in dependence upon the temperature. This means that atoms and molecules absorb photons of different frequencies in dependence upon the temperature, and this in turn results in different appearances of the absorption spectrum of a substance at different temperatures. FIGS. 5A and 5B illustrate two different spectra for sulphur dioxide, recorded at different temperatures in a 100 MWatt power plant straight through the flame. The differences are clearly apparent. By comparing a spectrum recorded by the apparatus according to the present invention, with spectra recorded during (or calculated for) known conditions, the temperature can be determined.

CONCENTRATION

The concentration is determined by means of the Lambert-Beer law $I = I_0 e^{-\rho l c}$ wherein I represents the intensity of the transmitted light, $I_0$ represents the intensity of the light source, $\rho$ represents the absorption cross-section of the substance in question, 1 represents the absorption distance, and c represents the concentration. For this determination of the concentration, however, the temperature must be known since the absorption cross-section is temperature dependent. However, the temperature can be readily determined by the method according to the present invention. The concentration thus determined is the mean concentration of the substance in question along the absorption distance. If the temperature is different at different points along the absorption distance, further information may be obtained.

PRESSURE

FIG. 6 illustrates an absorption profile, especially the broadening of the profile due to pressure and temperature. Curve A shows the true temperature contribution, so-called Doppler broadening. The half-width value of this curve is proportional to the root from the temperature. Curve B shows the appearance of the absorption profile upon pressure broadening. The half-width value of this curve is directly proportional to the pressure and proportional to the root from the temperature. These curves thus show the broadening phenomena separately. The actual absorption profile will be a combination of the two. If the temperature is known, one can thus determine the pressure as a function of the broadening of the absorption profile and vice versa.

NUMBER OF PARTICLES AND THEIR SIZE DISTRIBUTION

When the number of particles in a gas and the particle size distribution are to be determined, a spectrum of the entire optical region from UV to IR is recorded. The so-called Mie effect causes light of different wavelengths to be scattered differently against particles in the gas, and thus implies that different amounts of light in different wavelength regions will reach the receiving device. By comparing the intensity of the transmitted light in different wavelength regions in the spectrum, the particle size distribution can be determined, and by studying the level of the intensity of the entire wavelength region, the number of particles can be determined.

To be able to make the above-mentioned calculations it is a condition that a spectrum of sufficient accuracy can be recorded. This is made possible by the rapid sweeping and recording of the spectrum on the spectrometer output by means of a one-channel detector, and the greater the number of recordings, the higher the accuracy. More particularly, the noise decreases with the root from the number of recordings effected.

This technique has many advantages. It is far cheaper than the previously described laser-based method. Furthermore, a very high measuring accuracy can be obtained when measuring is effected on turbulent objects, by using a continuous light source and a one-channel detector, as well as by very rapid scanning of the spectrum. In many cases, the accuracy is better than can be achieved by other measuring techniques. It is a generic technique. The same apparatus may be used for measurements on different substances and for different applications. The measuring technique also is simple and reliable, and no skilled technicians are required for operating the equipment. Besides, the technique is suitable for long-term measurements since it need not be constantly supervised. It also is suitable for measurements at locations difficult of access since the light can be conducted to and from the point of measurement by means of optical fibres, which is not possible with the laser light of prior art technique. In addition, one and the same measuring apparatus can be used for monitoring several processes or several points of measurement in one process by conducting light from one or more lamps to the different points of measurement, and from the different points of measurement to the measuring apparatus proper by means of optical fibres, the apparatus being controlled to cyclically calculate the parameters of the different measurements. If several absorption distances are recorded simultaneously in different directions through the object of measurement, three-dimensional maps of the required measuring values can be generated by tomography.

The present invention is intended for real-time monitoring of and measuring in combustion processes, especially flames, and in all processes where high temperatures prevent the use of conventional technique. The present invention also is intended to function as a transucer for controlling processes of the above-mentioned type. Examples of applications are the heat-generating and power industries (combustion of various fuels, flame monitoring), chemical process industries (temperature monitoring in hydrochloric acid furnaces), the paper and pulp industry (determination of particle content, detection of gases at high temperatures), the iron and steel industry (temperature measurement in furnaces and converters, analysis of heavy elements in gas flows), the automobile industry (exhaust gas analysis, especially in connection with catalytic exhaust gas purification), etc.

The present invention naturally is not restricted to the embodiments illustrated, and many modifications can be made within the scope of the appended claims.

For example, the technique according to the present invention has been described with reference to an embodiment in which a lamp is used as the light source and an absorption spectrum is recorded by means of the light transmitted through the object of measurement. It is, however, also possible to record absorption spectra by means of the reflected light. Furthermore, the actual object of measurement may be used as a light source, and a spectrum is recorded of the emitted light.

We claim:

1. A method for determining a parameter such as pressure, temperature or concentration of a gaseous substances present in combustion processes and other high temperature processes, comprising
   (a) transmitting spectral broad-band, continuous light towards the gaseous substances, a part of the light being absorbed by the gaseous substances and a part of the light being transmitted through said gaseous substance;
   (b) spectrally dividing the transmitted light, whereby the absorption spectrum of the gaseous substances is obtained;
   (c) recording the absorption spectrum of the gaseous substances in a studied wavelength range a large number of times, each recording taking place sequentially by sweeping the absorption spectrum relative to a single-channel detector and for such a short time that the total intensity of the entire wavelength range is constant during each recording;
   (d) generating the means value of the recorded absorption spectra; and
   (e) calculating the parameter on the basis of the appearance of the mean absorption spectrum and absorption spectra determined for known conditions.

2. An apparatus for determining a parameter such as pressure, temperature or concentration of a gaseous substances present in combustion processes and other high temperature processes, comprising
   (a) a spectral broad-band, continuous light source adapted to transmit light towards the gaseous substances;
   (b) means for spectrally dividing the light transmitted from said light source and through said gaseous substances, to obtain the absorption spectrum of said gaseous substances;
   (c) recording means for sequentially recording a large number of times, the absorption spectrum of said gaseous substances in a studied wavelength range, said recording means comprising a one-channel detector whose output signal is proportional to the intensity of the received light and means for sweeping the absorption spectrum relative to said one-channel detector, and said recording means being adapted to perform each recording in such a short time that the total light intensity of the studied wavelength range is constant;
   (d) a mean value generator for generating the mean value of the spectra recorded by said recording means; and
   (e) calculating means for calculating the parameter.

3. An apparatus as claimed in claim 2, wherein said means for sweeping the absorption spectrum in relation to said one-channel detector is a rotary disk which is provided along its periphery with slits extending parallel to the axis of rotation of said disk, and which carries in its center a means for spectral division of the light and focusing the light against said slits.

* * * * *

UNITED STATES PATENT AND TRADEMARK OFFICE
CERTIFICATE OF CORRECTION

PATENT NO. : 4,790,652

DATED : December 13, 1988

INVENTOR(S) : Uneus, et al.

It is certified that error appears in the above-identified patent and that said Letters Patent is hereby corrected as shown below:

Column 1, line 36, second "," should not be there;

Column 5, line 36, "means" should be --mean--;

line 36, after "spectra" should be a --,--;

Column 5, lines 36-39, "re-corded under known conditions. and for controlling the rotary mirror 7 as well as reference spectra recorded under known conditions." should read --for calculating the required parameters, and for controlling the rotary morror 7 as well as reference spectra recorded under known conditions.--;

Column 7, lines 31 and 33, "p" symbol should be --$\sigma$-- symbol;

Column 7, line 34, "1" (numeral) symbol should be --l-- (letter 'l') symbol;

Column 8, line 53, "transucer" should be --transducer--.

Signed and Sealed this

Twenty-seventh Day of June, 1989

Attest:

DONALD J. QUIGG

Attesting Officer

Commissioner of Patents and Trademarks